United States Patent [19]

Lipthay et al.

[11] 4,122,350
[45] Oct. 24, 1978

[54] ADJUSTABLE COLLIMATOR FOR MAMMOGRAPHY

[76] Inventors: Julius Lipthay, 171 Biltmore Blvd.;
Dogan Kizilay, 310 Bayview Ave.,
both of Massapequa, N.Y. 11758

[21] Appl. No.: 853,131
[22] Filed: Nov. 21, 1977
[51] Int. Cl.² .............................................. G21F 5/04
[52] U.S. Cl. ................................... 250/505; 250/511
[58] Field of Search ................ 250/505, 511, 512, 513

[56] References Cited

U.S. PATENT DOCUMENTS

| | | | |
|---|---|---|---|
| 3,448,270 | 6/1969 | Peyser | 250/511 |
| 3,609,370 | 9/1971 | Peyser | 250/511 |
| 3,997,794 | 12/1976 | York | 250/511 |

Primary Examiner—Craig E. Church
Attorney, Agent, or Firm—Bauer, Amer & King

[57] ABSTRACT

An adjustable collimator is provided for use in mammography in which there is a mounting ring for securing the collimator to an x-ray source; a collimating cone having a plurality of leaves, each pivotably secured at one end thereof to said mounting ring and positioned in overlapping relationship to one another to define at their opposite ends a substantially kidney shaped opening through which x-rays may be directed to a female breast positioned below said cone; and a collar positioned about and capturing the plurality of leaves and to be raised and lowered along the leaves relative to said mounting ring to adjust the size of the opening.

14 Claims, 10 Drawing Figures

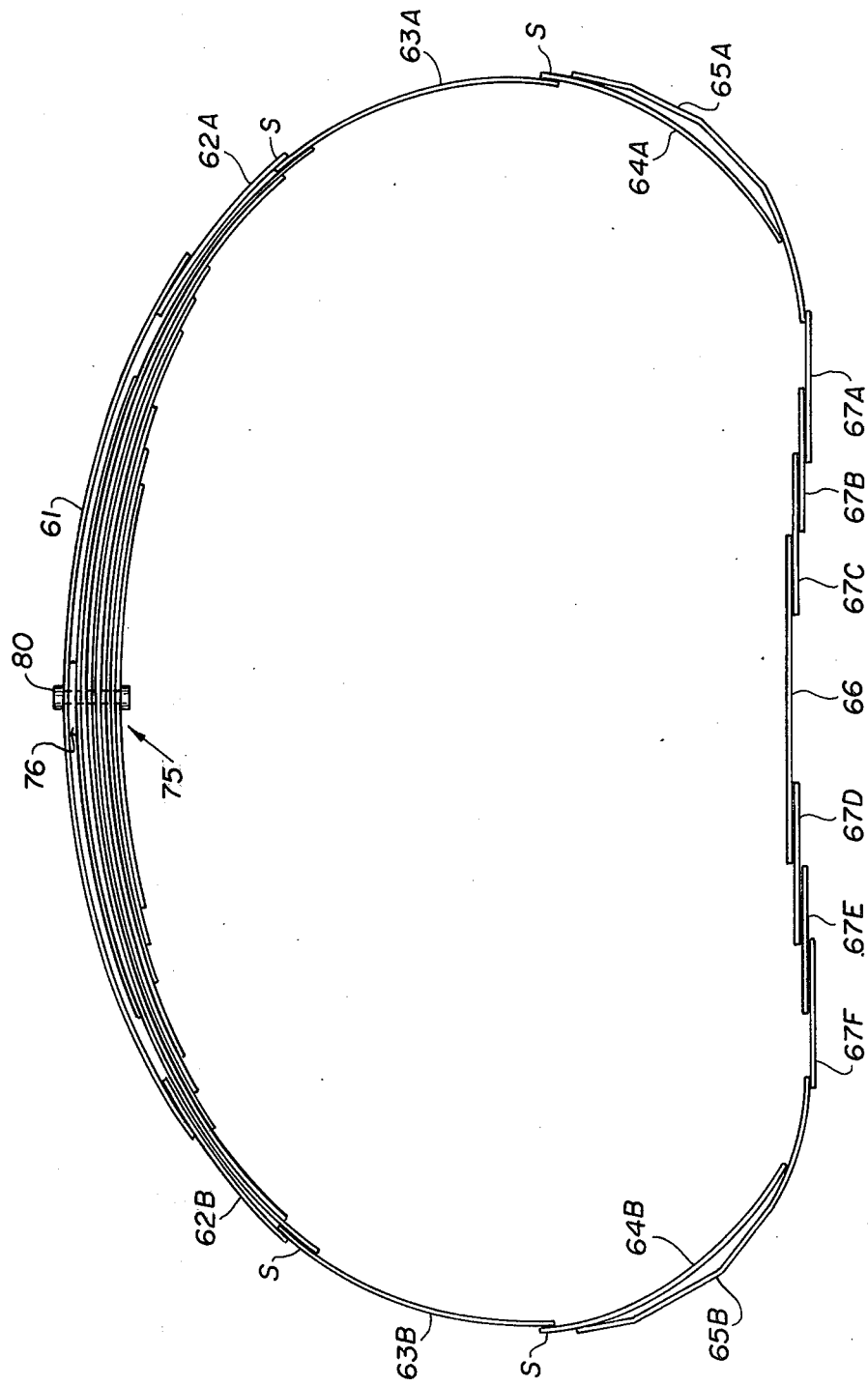

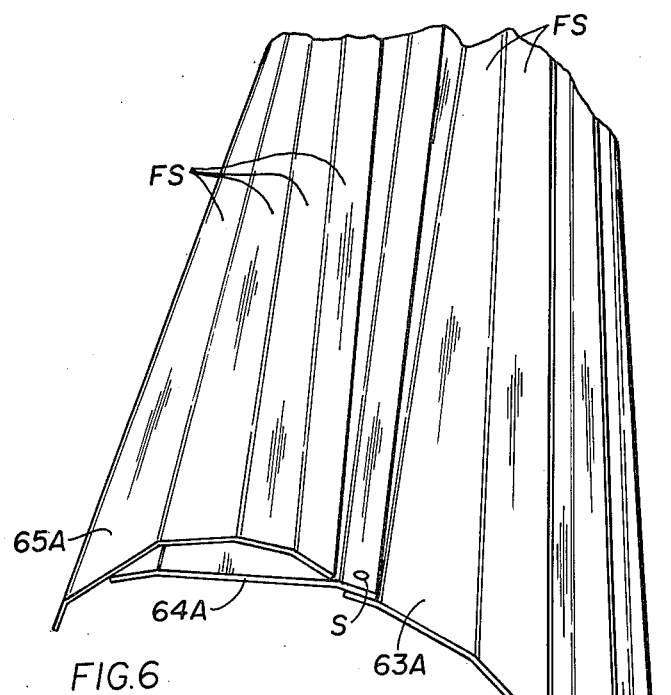
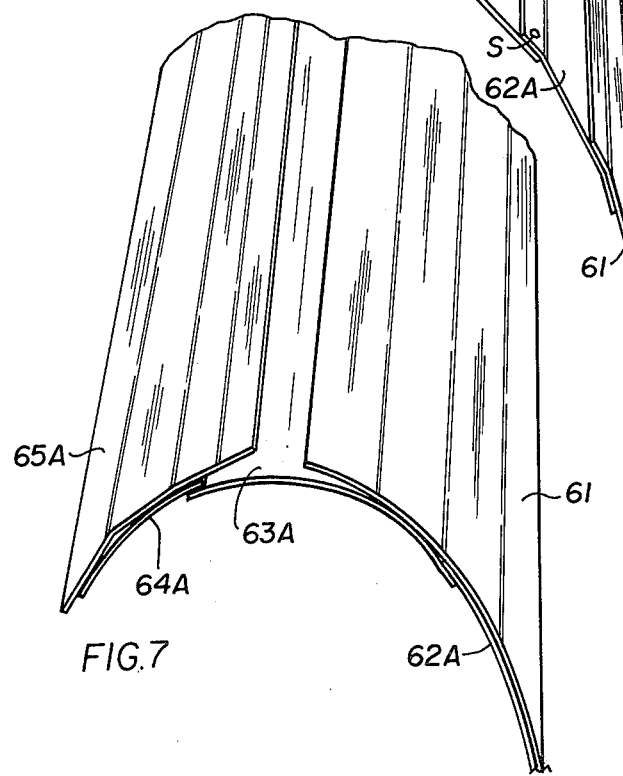

ADJUSTABLE COLLIMATOR FOR MAMMOGRAPHY

BACKGROUND OF THE INVENTION

The present invention relates generally to an adjustable collimator for mammography and, more particularly, to an adjustable collimator for use with different size and shaped female breasts which minimizes fogging problems in the x-ray film due to secondary radiation and which eliminates the possibility of radiation scattering to tissue other than breast tissue.

Mammography is the x-ray technique used to detect and diagnose anomolies of the female breast including, for example, cancerous lumps or nodules. As the field has developed in recent years and newer and more advanced techniques have been implemented, a frequent, reoccurring problem is how one can utilize a standard mammography x-ray unit to accommodate a wide variety of breasts of varying size and shape. Typical mammography units described, for example, in U.S. Pat. No. 3,824,397, which issued to M. Bauer et al. on July 16, 1974, and U.S. Pat. No. 3,609,355, which issued to K. Schwarzer on Sept. 28, 1971, use an x-ray source which is collimated for mammography.

A collimating device is generally provided to restrict the x-rays to the breast. The collimator is designed to fit closely over the breast and to rigidly confine the x-rays within it to prevent scattering with resultant possible radiation damage to other parts of the patient. Additionally, the collimator functions to prevent secondary radiation which can fog the x-ray film. As such, it is very important that the collimator fit very closely and even tightly against the breast to prevent leakage and/or the introduction of secondary radiation and yet include the entire breast in the x-ray.

The problem presented here is that there are many different size and shaped breasts and a collimator which fits tightly against one may not fit as well against another. Accordingly, this has, heretofore, necessitated the stocking by a physician or x-ray laboratory of a number of collimators of different sizes and shapes which could be interchangeably mounted on a standard mammography machine. This has, as can be expected, resulted in an increased expense and a storage problem for the physician or laboratory as well as increasing the time required to perform the mammography since a particular breast would first have to be sized and an appropriate sized and shaped collimator would then have to be selected and mounted.

Attempts have, heretofore, been made to provide adjustable collimators for x-ray applications other than for mammography. For example, U.S. Pat. No. 3,448,270, which issued to L. Peyser on June 3, 1969, teaches an x-ray collimator having a plurality of pivotably movable shutter elements arranged in pyromidal fashion. Similarly, U.S. Pat. No. 3,609,370, which also issued to L. Peyser on Sept. 28, 1971, is directed to a collimator having a number of shutter elements or leaves. Neither of these collimators, however, is readily adaptable for use in mammography and both require extensive apparatus to effect re-adjustment of the cone.

Against the foregoing background, it is a primary objective of the present invention to provide an adjustable collimator to accommodate virtually any size and shaped breast.

It is another objective of the present invention to provide an adjustable collimator for mammography which can be used in conjunction with conventional mammography machines.

It is still another objective of the present invention to provide an adjustable collimator which is resistant to jamming and which can be easily readjusted to a different size.

It is yet another object of the present invention to provide an adjustable collimator which prevents leakage of x-rays.

SUMMARY OF THE INVENTION

To the accomplishment of the foregoing objects and advantages, the present invention, in brief summary, comprises: an adjustable collimator for use in mammography. The collimator includes a mounting ring for securing the collimator to an x-ray source; a plurality of leaves; each of said leaves pivotably secured at one end thereof to the mounting ring. The leaves are positioned in overlapping x-ray-tight relationship to one another to define at their ends opposite the mounting ring a substantially kidney-shaped opening through which x-rays may be limited against a subject. A collar is further provided about and capturing the plurality of leaves such that upon raising and lowering the collar relative to the mounting ring along the longitudinal extent of the leaves, the size and shape of the opening will be varied.

DESCRIPTION OF THE DRAWINGS

The foregoing and still other objects and advantages of the present invention will be more apparent from the following detailed explanation of the invention in connection with the accompanying drawings wherein:

FIG. 5A is a bottom view of the collimator in a fully opened position;

FIG. 6 is a partial perspective bottom view of the collimator in a fully opened position; and FIG. 7 is a partial perspective bottom view of the collimator in its closed, unexpanded position.

DESCRIPTION OF THE PREFERRED EMBODIMENTS

Figure 1:
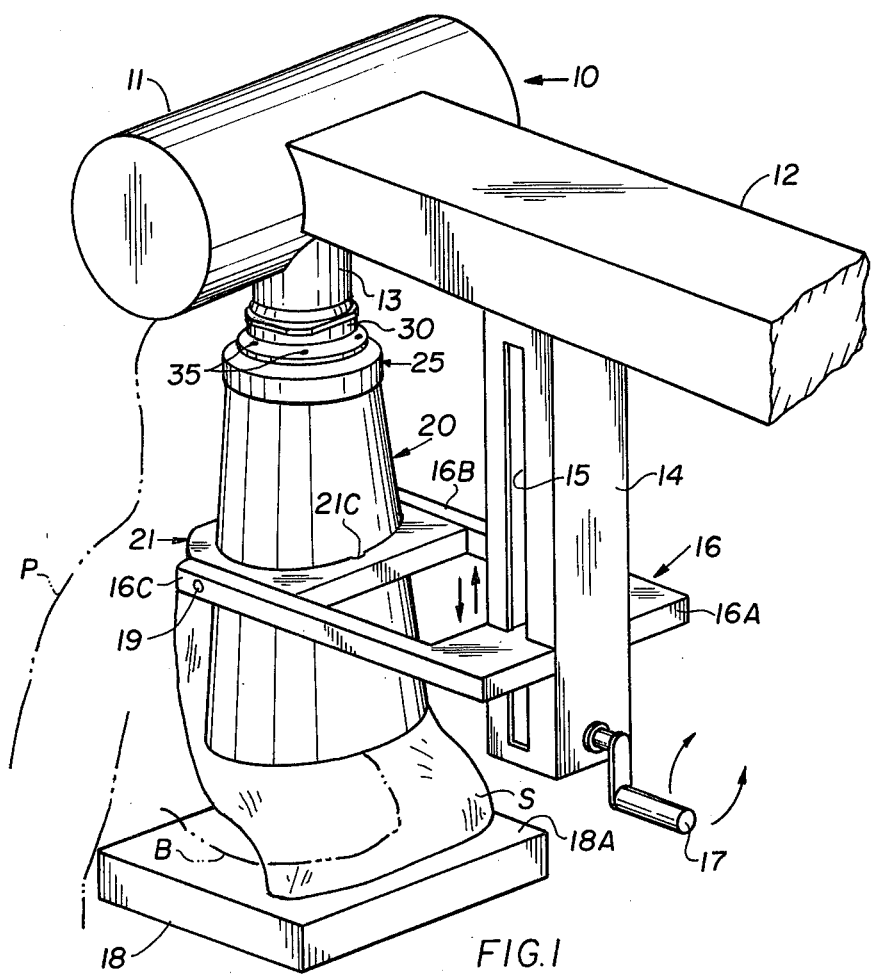
FIG. 1 is a perspective illustration of the collimator of the present invention mounted on a mammography machine in an operational position relative to a patient.
Figure 2A:
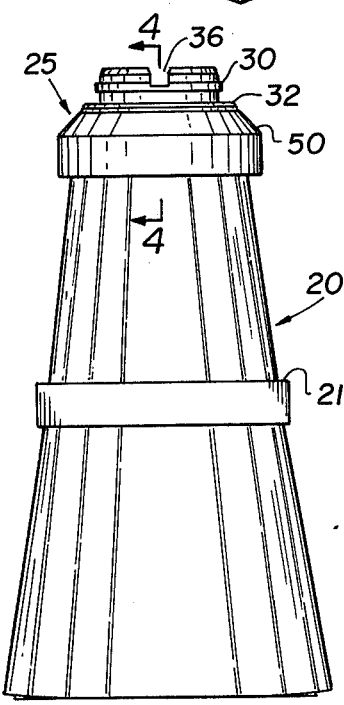
FIG. 2A is a front elevational view of the collimator of the present invention.
Figure 2B:
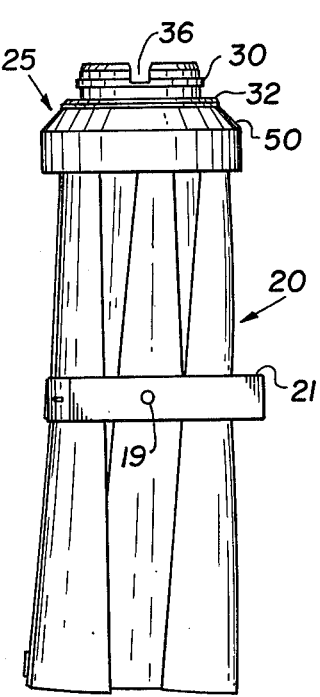
FIG. 2B is a side elevational view thereof.
Figure 2C:
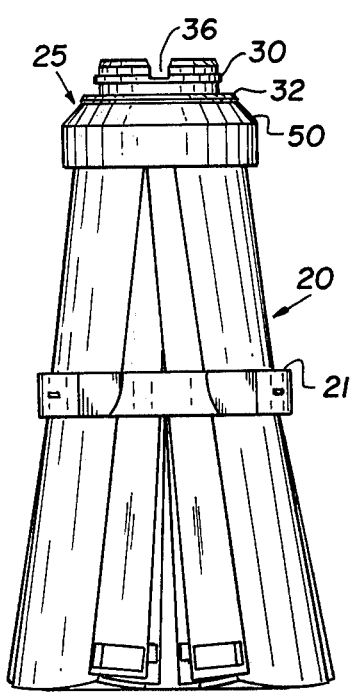
FIG. 2C is a rear elevational view thereof.

Referring now to the drawings and, in particular, to FIG. 1 thereof, the collimator of the present invention referred to generally by reference numeral 20 is shown in relationship to an x-ray machine 10 used for mammography. X-ray machine 10 includes an x-ray source 11 having an outwardly extending arm 12 and, at right angles to the arm 12, a downwardly extending exit 13 through which a stream of x-rays is emitted from the source 11 to effect mammography. The collimator 20 is securely but releasably mounted to exit 13. A downwardly extending jack 14 is provided from arm 12 such that the jack 14 and the collimator 20 are in substantial parallel alignment.

Jack 14 includes a groove or track 15 through the thickness thereof, said jack 15 extending substantially along the entire vertical extent of the jack 14. A collar support 16 is slidably mounted within track 15 and is adapted to be raised and lowered along track 15 by conventional cranking means (not shown) effected by manual rotation of crack handle 17. It will be appreciated, of course, that collar support 16 may be raised or lowered by other means including, for example, an electric motor.

Collar support 16 includes a base portion 16A captured within track 15 and two outwardly extending opposed arm portions 16B and 16C. A collar 21 which encircles collimator 20 and which is used to control the size and shape of the collimator 20 is pivotally secured at 19 between the two arm portions 16B and 16C. Thus, by raising and lowering collar support 16 by crank 17, the size and shape of the collimator 20 may be adjusted.

Box-shaped, plate support 18 is provided directly beneath the collimator 20 such that the patient P, illustrated in broken lines, is able to place the breast B to be x-rayed on its flat upper surface 18A under the collimator 20. A sheet S of non-conductive material, i.e., a thermoplastic, is draped from the collimator 20 and is placed between the collimator 20 and the breast to protect the breast from contact with the collimator.

Figure 3:
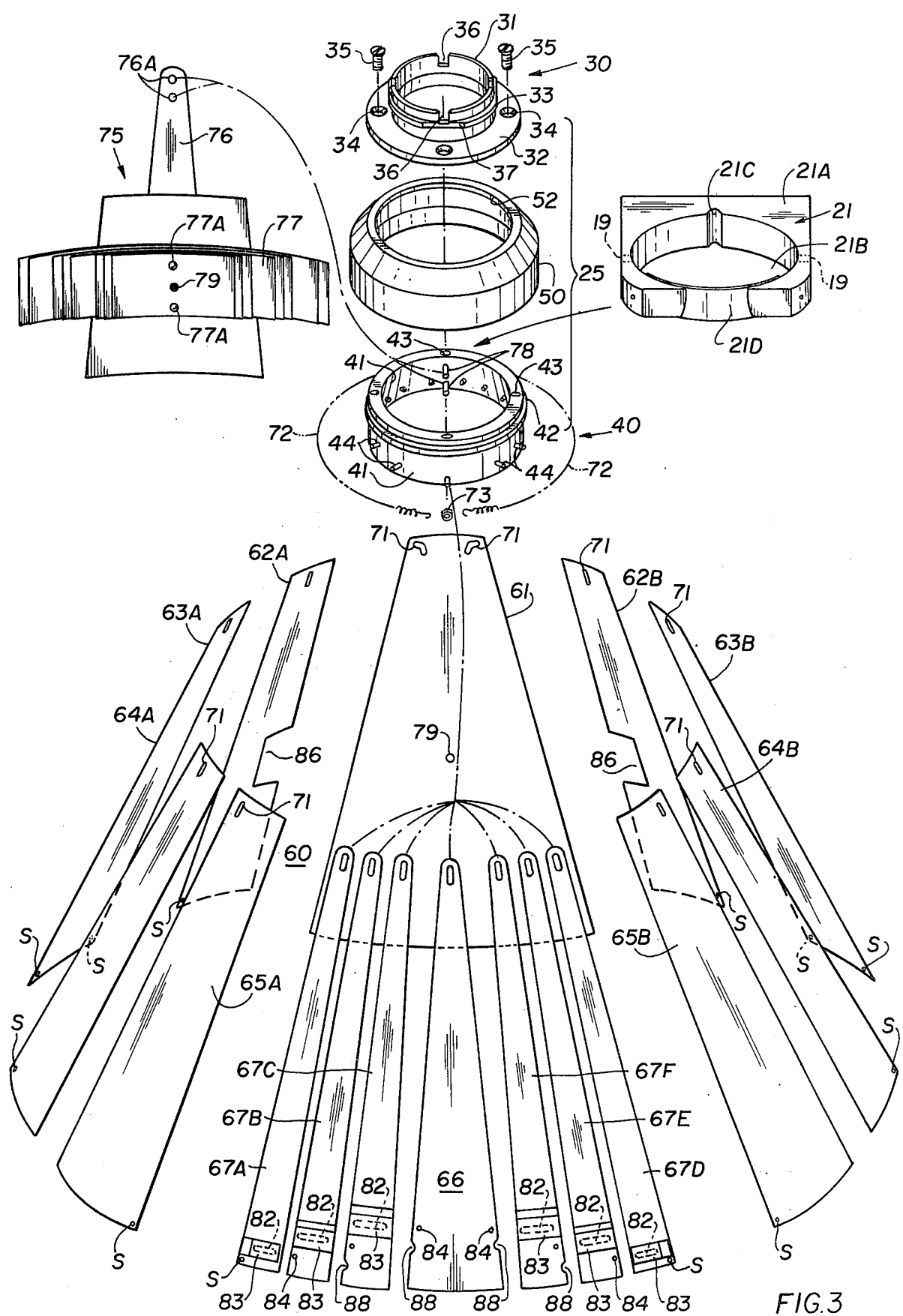
FIG. 3 is an exploded breakaway perspective view of the collimator.

Collar 21, as shown in FIG. 3, includes a generally C-shaped body portion 21A defining a central aperture 21B which encircles and captures the collimator 20. The body portion of the collar 21 includes a notch 21C and a metal strap portion 21D substantially enclosing the C-shaped aperture. The collar 21 is pivotally secured at 19 to the two arm portions 16B and 16C of the collar support 16. Since the central aperture 21A of the collar support 21 is of a fixed diameter, as it is moved up and down by the crank means on the jack 14, it serves to permit the varying adjustment of the size and shape of the collimator 20 as will be described in greater detail.

The collimator 20, shown in greater detail in FIGS. 2A, 2B, 2C and 3, includes at one end thereof a connecting device 25 including a mounting ring 30 interconnected to a leaf mounting ring 40 and covered by a shroud 50. Mounting ring 30, as shown in FIG. 3, includes a tubular center portion 31 with a flange 32 at one end thereof and a locking ring 33 extending circumferentially about the center portion 31 spaced approximately midway between the flange 32 and the opposite end of the center portion 31. Flange 32 includes a number of apertures 34, preferably four, for receiving mounting screws 35 for use in mounting the mounting ring 30 to the leaf mounting ring 40.

At least two, and preferably four, locating slots 36 are provided on the non-flanged end of the center portion 31 to insure proper alignment of the mounting ring 30 when mounting it on the exit 13 of the x-ray machine. Mounting of the collimator 20 to the x-ray machine 10 is effected by insertion of the non-flanged end of mounting ring 30 into the exit 13 of the x-ray machine such that slots 36 are properly aligned with stops (not shown) on the inner diameter of exit 13 and one or more flats 37 are aligned with correspondingly shaped openings in the exit 13. The mounting ring 30 is then rotated until the locking ring 33 engages complementary locking means (not shown) on the inside diameter of the exit 13 to prevent its downward displacement from the exit 13.

Leaf mounting ring 40 includes a tubular axially extending center portion 41 having a radially directed flange 42 at its upper end. Flange 42 includes a number of apertures 43 through its thickness for receiving the mounting screws 35 of the mounting ring 30 in order to secure the mounting ring 30 to the leaf mounting ring 40. A plurality of circumferentially spaced outwardly extending radially directed leaf pins 44 are proximately spaced about center portion 41 to loosely engage and releasably secure a plurality of leafs referred to generally by reference numeral 60. Threaded flange 42 is adapted to threadably engage an internally threaded portion 52 of shroud 50 to form connecting device 25.

Collimator wings or leaves 60, as shown in FIG. 3, include a main posterior leaf 61, at least two oppositely disposed posterior lateral leaves 62A and 62B, at least two opposite radial lateral leaves 63A and 63B, at least two opposed anterior lateral leaves 64A and 64B, at least two opposite anterior corner leaves 65A and 65B, at least one main anterior leaf 66 and at least a plurality of six anterior floating leaves 67A, 67B, 67C, 67D, 67E and 67F. Each of the aforedescribed leaves is elongated longitudinally to extend for the full length of the cone 20 and each tapers from its wider bottom where it forms a part of the cone opening toward its narrower top.

Figure 5B:
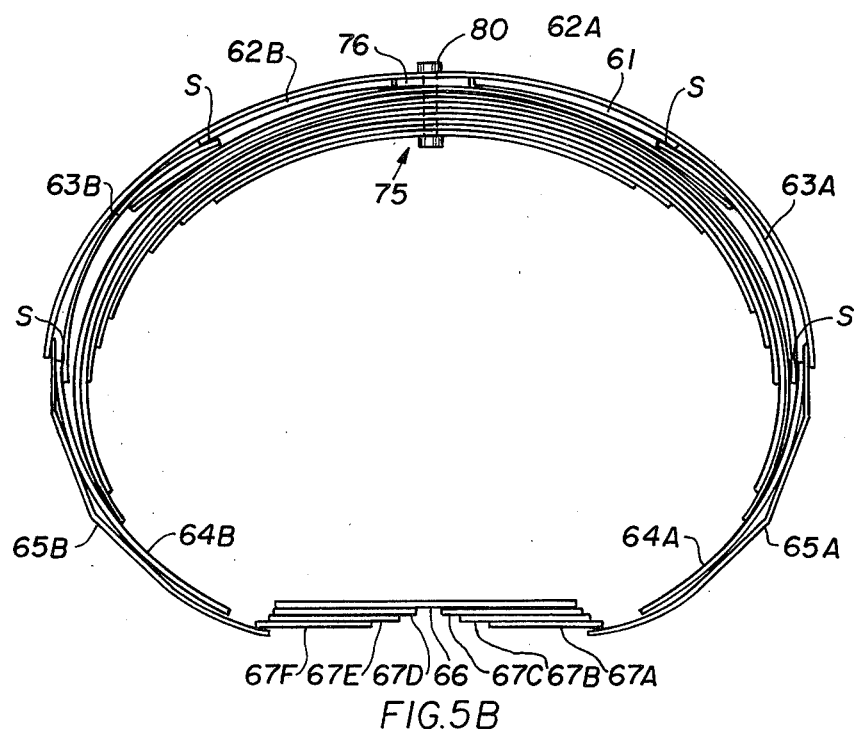
FIG. 5B is a bottom view of the collimator in a substantially closed position.

As shown in greater detail in FIGS. 3 and 5A and 5B, the main posterior leaf 61 is positioned directly opposite the main anterior leaf 66. Positioned in both a clockwise and counterclockwise direction from the main posterior leaf 61 to the main anterior leaf 66 are, in each direction, at least one posterior lateral leaf 62, at least one medial lateral leaf 63, at least one anterior lateral leaf 64, at least one anterior corner leaf 65 and at least one anterior floating leaf 67. It is preferred that at least three anterior floating leaves 67 be positioned on each side of the main anterior leaf 66. Those leaves clockwise to or at the right of leaf 61 are identified by the letter B while those opposite are identified by the letter A.

Each of the leaves are of a general fan-shape tapering outwardly from a generally narrower upper width to a generally greater lower width. In this manner, the collimator 20 assumes a general cone shape with a smaller inside diameter at its upper portion adjacent connecting device 25 to a larger inside diameter at the lower opening. The anterior corner leaves 65A and 65B are generally curved and, to effect this, may be segmented. All other leaves are of a lesser curvature. All leaves overlap adjacent leaves thus preventing x-ray leakage from between them.

Figure 4:
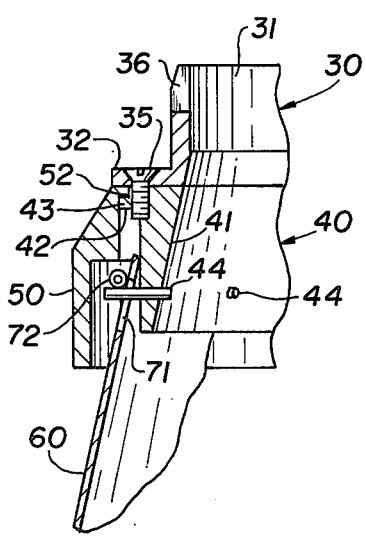
FIG. 4 is a sectional view taken along line 4—4 of FIG. 2A.

Each leaf is loosely pivotably connected to the leaf mounting ring 40 by the leaf pins 44 on the center portion 41 which engage the leaves 60 by passage through at least one aperture 71 included in the narrower upper width of each leaf and which aperture is larger than its engaging pin. The main posterior leaf 61 includes two substantially 7-shaped apertures 71 at its narrower upper width. All the apertures 71 are somewhat elongated or slot like and are of a greater dimension than the leaf pin 44 which it is adapted to receive, thus providing a certain lost motion or pivotable engagement of the leaves. This lost motion permits sufficient movement of the leaves 60 to effect expansion and contraction of the cone opening. The leaves 60 are retained in place, as shown in FIGS. 3 and 4, by a spring 72 which encircles the leaves 60 above the plurality of pins 44. Spring 72 is connected to at least one pin 44 by a locking nut 73.

As shown in FIG. 3, a leaf spring assembly 75 is provided having a longitudinally elongated rear support spring 76 and a plurality, preferably 10, of horizontally extending leaf springs 77, each of different length, secured to the supporting spring 76 by rivets 77A. Apertures 76A extend through the top of rear support spring 76 for affixing the assembly 75 to the leaf mounting ring 40 by screws 78 or other securing means. An aperture 79 is provided through both the leaf springs 77 and the rear support spring 76 for affixation of the whole assembly 75 to the main posterior leaf 61 by a rivet 80, as seen in FIGS. 5A and 5B. Leaf spring assembly 75 provides outward tension in varying amounts against each of the main posterior leaf 61, the posterior lateral leaves 62, the medial posterior leaves 63, the anterior lateral leaves 64 and the anterior corner leaves 65 thus, in the absence of any restraint, normally urging the cone 20 into its maximum open position. This internal tension applied by the springs against the leaves also urges the leaves into engaging overlapping light-tight contact that serves to prevent any x-ray leakage from between them.

As shown in FIG. 3, each of the anterior floating leaves 67 include at their wider lower end at least one elongated slot 82 and an externally projecting pin member 84 adapted to engage the slot 82 of an adjacent floating leaf 67 in order to adjustably secure each floating leaf 67 to its adjacent floating leaf. A cover or shield 83 may be provided over each slot 82 to prevent x-rays from scattering beyond the collimator through the slots. Pin members 84 are provided on the main anterior leaf 66 in order to adjustably secure it in the slots 82 of the respective adjacent floating leaves 67C and 67D. The pins 84 of the leaves 67C and D engage with the next adjacent slots of leaves 67B and E respectively whose pins 84 engage in the slots of leaves 67A and F respectively.

The outermost floating leaves 67A and 67F are permanently affixed, preferably by spot welding at S to their adjacent anterior corner leaves 65A and 65B, respectively. The posterior lateral leaves 62A and 62B, medial lateral leaves 63A and 63B and anterior lateral leaves 64A and 64B are also all permanently affixed, at their lower ends, to their next adjacent leaves, preferably by spot welding at points S as is more clearly seen in FIG. 6.

FIGS. 5A and 5B and FIGS. 6 and 7 show, in greater detail, the maximum and minimum shapes which the collimator cone may assume since the adjacent posterior lateral leaves 62A and 62B, medial lateral leaves 63A and 63B and anterior lateral leaves 64A and 64B are all permanently affixed to one another as are the outermost floating leaves 67A and 67F to their adjacent anterior corner leaves 65A and 65B, respectively.

In operation, a downward motion of the collar 21 along the collimator leaves of the cone 20 will cause the posterior lateral leaves 62A and 62B to compress inwardly toward the main posterior leaf 61; the anterior corner leaves 65A and 65B to compress inwardly toward the anterior lateral leaves 64A and 64B and the anterior floating leaves 67 to compress and collapse among themselves and along the main anterior leaf 66, all in opposition to the outward urging of the spring assembly 75. Therefore, as shown in the prospective partial bottom view of FIG. 7 the view of FIG. 5B the cone 20 is compressed such that main posterior leaf 61 and anterior corner leaf 65A form an outer tier. The anterior lateral leaf 64A, the medial lateral leaf 63A and the posterior lateral leaf 62A form an inner tier protecting against the escape of any radiation. To provide for the fullest possible collapse of the cone 20, the leaves 62A and B are notched at 86 to accommodate the rivet 80. In like manner the leaves 66 and 67C and D are notched at 88 to accommodate the pins 84 to receive them when the leaves fan closed toward each other. The notch 21C on the collar permits the collar to move relative to the leaf 61 and to enable the notch to pass unobstructedly over the head of the rivet 80.

Referring to FIGS. 6 and 7, it will be seen that the posterior lateral leaf 62A (62B), the medial lateral leaf 63A (63B) and the anterior lateral leaf 64A (64B) are provided with relatively flat surfaces FS that merge with each other and narrow in taper along the length of the cone 20. Each of these flat surfaces extends longitudinally for substantially the full length of the respective leaf up to and into the connecting device 25. The anterior corner leaf 65A (65B) is similarly provided with tapering substantially flat surfaces FS which are directed longitudinally of the leaf, but are skewed in their relationship.

The reason for the skewed arrangement of the flat surfaces of the anterior corner leaf 65 is to enable this leaf member to ride over the anterior lateral leaf 64 in the manner as is shown in FIG. 7 when the cone is collapsed or reduced at its opening to assure that the opening will retain the necessary and desired kidney shape. Unless the surfaces FS of the anterior corner leaf 65 are tapered and skewed relative to each other, during the opening and closing movement of the leaves the kidney shape of the exit opening of the cone 20 will become more circular. Hence, by providing the leaves 62, 63, 64 and 65 with elongated flat surfaces and by further providing the leaf 65 with its flat surfaces tapered and skewed in the manner as illustrated in FIGS. 6 and 7, the exit opening of the cone will always retain its desired kidney shape.

In the opposite manner, upward movement of the collar relieves the constriction on the leaves and enables them to fan open in response to the urging of the spring assembly 75. When the leaves separate and open, they assume the expanded condition as shown in FIGS. 5A and 6. The opening and closing fan-like movements of the leaves of the cone are supported at the pivot pins 44 and between the leaves 66 and 67 by the pin and slot connections 84 and 82. It will be noted that through all positions of relative movement of the cone the exit opening thereof always assumes a shape that is most closely related in cross-section to the top view of a female breast that is positioned flat on the plate holder 18.

This shape is probably best defined as being substantially kidney shaped, although not necessarily limited to that definition. Hence, reference to the kidney shape should not be limited in the strictest sense to that definition, but rather one of approximately that configuration. Thus, regardless of the movements of the leaves relative to each other, the exit opening will always assume and retain substantially the same shape which will vary only in size in response to the operation of the ring 21. Hence, the x-rays are always concentrated on the full area of the breast with a minimum of loss to the area surrounding the breast regardless of the size of the breast, thereby producing an x-ray image of sharp definition with minimal scatter.

Having thus described the invention with particular reference to the preferred forms thereof, it will be obvious that various changes and modifications may be made therein without departing from the spirit and scope of the invention as defined in the claims.

What is claimed is:

1. An adjustable collimator for use with an x-ray apparatus for the production of images of a female breast, said collimator comprising:

>connecting means for securing said collimator to an apparatus having an x-ray source;
>
>a collimator cone having a plurality of longitudinally extending leaves, each of said leaves secured at one end thereof to said connecting means and positioned along their longitudinal extent in overlapping relationship to one another in order to define at their opposite end an exit opening shaped substantially to that of a female breast and through which x-rays may be restricted toward a female breast;
>
>a collar positioned about the leaves of said collimator cone to be raised and lowered along the longitudinal extent thereof to adjust the size of said opening without affecting the shape thereof;
>
>and urging means normally applying a separating force to certain of said leaves to enlarge said exit opening.

2. A collimator of claim 1 wherein said connecting means includes means to releasably connect the same to the apparatus having an x-ray source.

3. A collimator of claim 1 wherein said leaves are mounted to said connecting means with a lost motion connection and each of said leaves is engaged by said collar in response to the force applied by said urging means.

4. A collimator of claim 3, certain of said leaves being free of the direct application of the separating force and having a floating connection with each other.

5. A collimator of claim 1, said exit opening being of substantially kidney shape.

6. An adjustable collimator for use in mammography of different sized female breasts comprising:

>a plurality of longitudinally extending leaves each in x-ray tight overlapping relationship to form an exit opening with certain of said leaves being connected with adjacent leaves for conjoint movement with each other and certain others of said leaves being separately movable relative to adjacent leaves;
>
>means connecting said leaves together at one of their ends and for relative movement thereto;
>
>means applying a force to certain of said leaves to urge the same into separation from each other;
>
>and means about said leaves to restrict the separation of the leaves in response to the force applied to certain of said leaves and being movable along the length of said leaves to vary their relative separation and to adjust the size of said exit opening of said collimator without affecting the shape thereof.

7. An adjustable collimator as in claim 6,
and selected shape of said exit opening approximating substantially the shape of a flattened female breast.

8. An adjustable collimator as in claim 7,
said shape being substantially kidney shape.

9. An adjustable collimator as in claim 7,
said certain ones of said other leaves having pin and slot engagement with next adjacent leaves to enable a limited free floating movement therebetween.

10. An adjustable collimator as in claim 6,
certain of said leaves having a plurality of longitudinally extending flat surfaces skewed out of line of the longitudinal extent of the respective leaves.

11. An adjustable collimator as in claim 6,
said force applying means including a plurality of flat springs connected with at least one of said leaves and applying a separating force to leaves adjacent to and on opposite sides of said one of said leaves.

12. An adjustable collimator as in claim 11,
said means connecting said leaves together being a lost motion connection.

13. An adjustable collimator as in claim 11,
said means to restrict the separation of said leaves being a collar encircling said leaves and movable upward along the length thereof to enable said leaves to expand relative to each other in response to said force applying means to enlarge said exit opening and downward therealong to move said leaves to constrict said exit opening.

14. An adjustable collimator as in claim 13,
and means pivotally connected with said collar to move the same up and down along said leaves.

* * * * *

UNITED STATES PATENT AND TRADEMARK OFFICE
CERTIFICATE OF CORRECTION

PATENT NO. : 4,122,350
DATED : October 24, 1978
INVENTOR(S) : Julius Lipthay and Dogan Kizilay It is certified that error appears in the above–identified patent and that said Letters Patent are hereby corrected as shown below:

IN THE CLAIMS:

Claim 9, line 2, change first "said" to --and--

Signed and Sealed this

Sixth Day of February 1979

[SEAL]

Attest:

RUTH C. MASON
*Attesting Officer*

DONALD W. BANNER
*Commissioner of Patents and Trademarks*